United States Patent
Watanabe (10) Patent No.: US 7,896,002 B2
(45) Date of Patent: Mar. 1, 2011

(54) MEDICINE DISCHARGE DEVICE AND CARTRIDGE MOUNTABLE THERETO

(75) Inventor: Shinji Watanabe, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 363 days.

(21) Appl. No.: 11/776,842

(22) Filed: Jul. 12, 2007

(65) Prior Publication Data

US 2008/0023001 A1 Jan. 31, 2008

(30) Foreign Application Priority Data

Jul. 31, 2006 (JP) .............................. 2006-208500
Jun. 6, 2007 (JP) .............................. 2007-150302

(51) Int. Cl.
*A61M 11/00* (2006.01)

(52) U.S. Cl. .......................... 128/200.14; 128/200.23; 128/202.22; 128/204.23

(58) Field of Classification Search ................ 600/538, 600/532, 533; 128/200.14, 200.16, 200.19, 128/203.15, 203.12
See application file for complete search history.

(56) References Cited

U.S. PATENT DOCUMENTS

| | | | |
|---|---|---|---|
| 4,984,158 A | | 1/1991 | Hillsman |
| 5,167,506 A | * | 12/1992 | Kilis et al. .................. 434/262 |
| 5,724,986 A | * | 3/1998 | Jones et al. .................. 600/538 |
| 5,839,429 A | * | 11/1998 | Marnfeldt et al. ...... 128/200.14 |
| 5,839,430 A | * | 11/1998 | Cama ..................... 128/200.14 |
| 5,894,841 A | | 4/1999 | Voges ..................... 128/203.12 |
| 5,924,994 A | * | 7/1999 | Harbrecht et al. ............ 600/532 |
| 6,629,524 B1 | | 10/2003 | Goodall et al. .......... 128/200.14 |
| 6,637,430 B1 | | 10/2003 | Voges et al. ............. 128/200.14 |
| 6,752,145 B1 | * | 6/2004 | Bonney et al. .......... 128/200.23 |
| 6,932,083 B2 | * | 8/2005 | Jones et al. ............. 128/200.23 |
| 2002/0090601 A1 | * | 7/2002 | Strupat et al. ................ 434/363 |
| 2007/0240706 A1 | | 10/2007 | Kobayashi et al. ...... 128/200.14 |
| 2008/0011292 A1 | | 1/2008 | Sugita et al. ............ 128/200.19 |

FOREIGN PATENT DOCUMENTS

| | | |
|---|---|---|
| JP | 2006-068508 | 3/2006 |
| JP | 2006-102970 | 4/2006 |
| WO | 95/01137 A1 | 1/1995 |
| WO | WO 00/50111 | 8/2000 |
| WO | 02/04043 A2 | 1/2002 |
| WO | WO 2006/013952 A1 | 2/2006 |

OTHER PUBLICATIONS

European Communication and Search Report dated Nov. 20, 2007, regarding Application No. 07111428.4-2310.

* cited by examiner

*Primary Examiner*—Steven O Douglas
*Assistant Examiner*—Colin Stuart
(74) *Attorney, Agent, or Firm*—Fitzpatrick, Cella, Harper & Scinto (57) ABSTRACT

A medicine discharge device configured to discharge medicine to be administered to a user, includes a mount portion configured to mount a medicine discharge cartridge, the medicine discharge cartridge having at least a medicine reservoir and a medicine discharge portion and being removable from the device; and a receiving circuit configured to receive an output signal sent from a sensor, the sensor being provided at the cartridge mounted at the mount portion and detecting an inhalation state.

9 Claims, 7 Drawing Sheets

MEDICINE DISCHARGE DEVICE AND CARTRIDGE MOUNTABLE THERETO

BACKGROUND OF THE INVENTION

1. Field of the Invention

The present invention relates generally to a medicine discharge device and a cartridge mountable thereto, the device being carried by a user and configured to discharge medicine to be inhaled by the user. In particular, the present invention relates to a technique for safely using a medicine discharge device for healthcare etc.

2. Description of the Related Art

A treatment for a user with the combination of a medicine discharge device that discharges medicine to be inhaled by the user and an information database such as an electronic medical chart is being realized. Such a medicine discharge device includes a storage unit for storing information related to an individual user, the information including information of user's medical chart and prescription. The medicine discharge device is a handheld device also serving as an inhaler that allows the user to inhale the medicine. The medicine discharge device has a discharge controller that controls the inhaler to discharge the medicine so that the user may inhale the medicine in accordance with the information of prescription (see International Publication Nos. WO95/01137 and WO02/04043).

With this medicine discharge device, an amount of medicine administered may be properly managed in accordance with the prescription. Accordingly, medical equipment such as a syringe is no longer necessary for the administration of the medicine. The user may operate the medicine discharge device easily without special knowledge, and would not feel the pain caused by the syringe.

Meanwhile, it is important for a medicine discharge device to properly administrate medicine. Because of this, the safety and reproducibility of the device are assumed; however, in fact, the intake of the medicine is trained according to inhalation of the user. For the efficient intake of the medicine, the user must learn a proper inhalation technique.

An example of a technique is provided in which a sensor for detecting an inhalation pattern is provided at a body of an inhaler so that the user can learn the proper inhalation technique. The sensor displays an inhalation pattern by using an aerosol containing dummy medicine, and provides visual and auditory biofeedback for the inhalation pattern (see U.S. Pat. No. 4,984,158).

When the inhalation pattern is detected for the learning of the proper inhalation technique, it is necessary to use a sensor with a sufficiently high accuracy. However, the detection and display of the inhalation pattern using such a sensor is not essential when actual inhalation is performed. The detection of the inhalation pattern during the actual inhalation merely provides the post-evaluation of the inhalation. The detection of the inhalation pattern is desired to be performed in training with no medicine discharged, so as to learn the proper inhalation pattern in the training on a daily basis. In such a case, although the user is expected to inhale the medicine in a manner learned by the training, a simple sensor for detecting the beginning of the inhalation may be provided at the body of the device rather than the highly accurate sensor.

The provision of the highly accurate sensor at the body of the device is a bottleneck in simplification of the configuration of the device.

Also, an air channel through which the discharged medicine is guided into the body of the user may have a negative pressure which is caused by the inhalation and varies with location. To detect the inhalation pattern, it is desired to provide the sensor at a portion near the discharge portion of the medicine (a portion having the same negative pressure as that of the discharge portion). However, it is difficult to provide the sensor in the above-described manner due to structural limitation.

SUMMARY OF THE INVENTION

The present invention provides a medicine discharge device capable of simplifying the configuration of a device body, detecting an inhalation pattern, and thus allowing a user to learn a proper inhalation technique.

According to an aspect of the present invention, a medicine discharge device configured to discharge medicine to be administered to a user, includes a mount portion configured to mount a medicine discharge cartridge, the medicine discharge cartridge having at least a medicine reservoir and a medicine discharge portion and being removable from the device; and a receiving circuit configured to receive an output signal sent from a sensor, the sensor being provided at the cartridge mounted at the mount portion and detecting an inhalation state.

According to another aspect of the present invention, an inhalation-training cartridge mountable onto a medicine discharge device configured to supply a discharge signal for discharging medicine to be administered to a user, includes a sensor configured to detect an inhalation state.

With the medicine discharge device according to the aspect of the present invention, the user can perform the inhalation training easily on a daily basis without an instruction given by a professional. In addition, the configuration of the device may be simplified with no additional expensive function provided at the device body. Further, since the sensor may be disposed near the actual discharge portion, the inhalation pattern may be properly detected.

Other features and advantages of the present invention will be apparent from the following description taken in conjunction with the accompanying drawings, in which like reference characters designate the same or similar parts throughout the figures thereof.

DESCRIPTION OF THE EMBODIMENTS

Preferred embodiments of the present invention will now be described in detail in accordance with the accompanying drawings.

Figure 1:
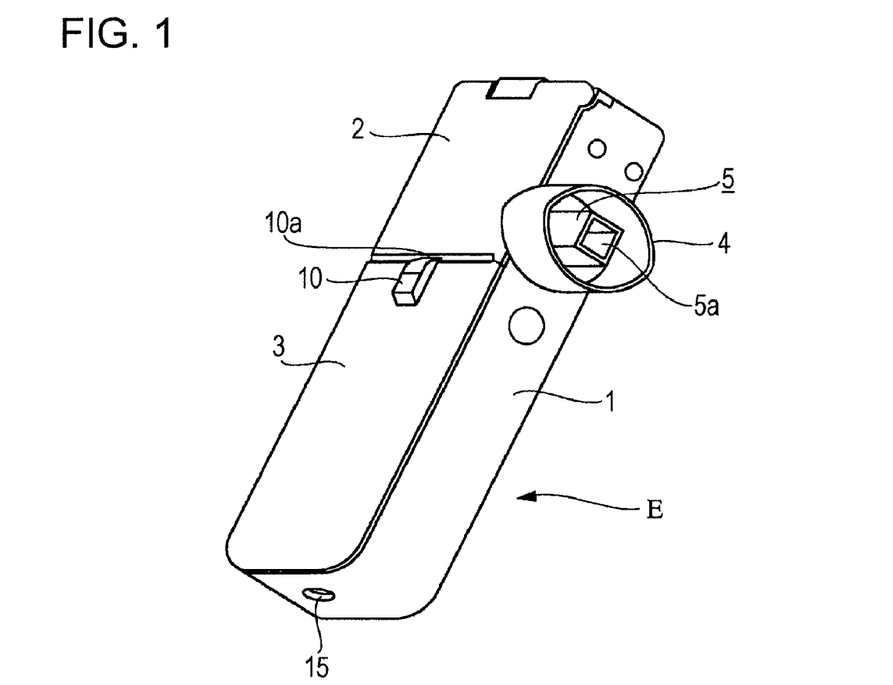
FIG. 1 is a perspective view showing an example of an inhaler using a medicine discharge device according to an embodiment of the present invention.
Figure 2:
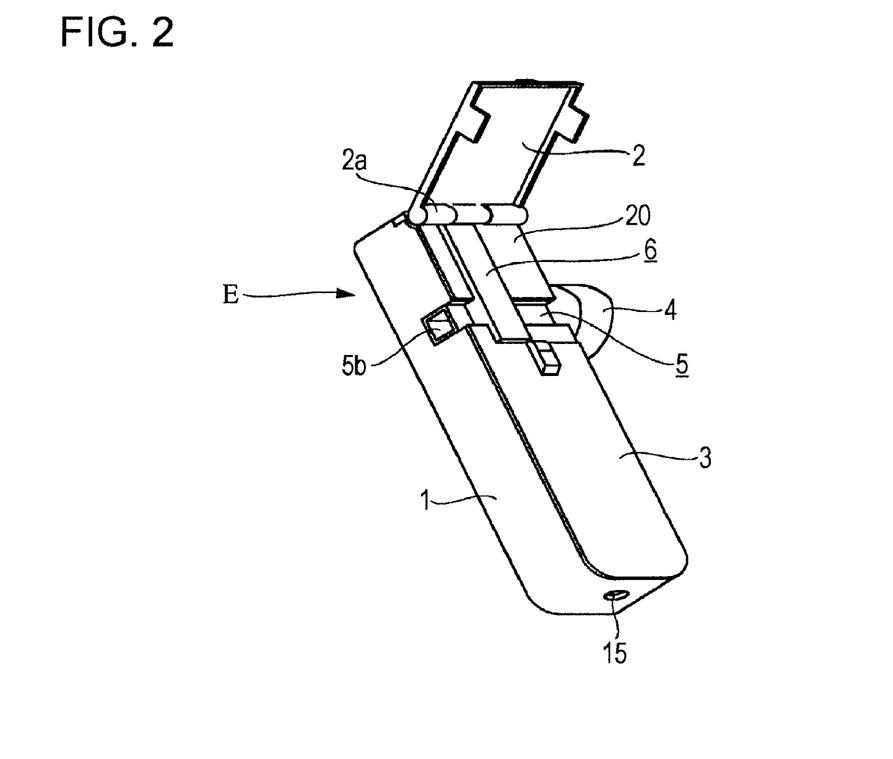
FIG. 2 is a perspective view showing the inhaler shown in FIG. 1 in a state where an access cover thereof is open.

FIG. 1 is a perspective view showing the appearance of an inhaler using a medicine discharge device according to an embodiment of the present invention. FIG. 2 is a perspective view showing the inhaler shown in FIG. 1 in a state where an access cover thereof is open.

An inhaler E of this embodiment includes a box-like housing body 1, and a front cover 3 and an access cover 2 at an open side of the housing body 1.

The front cover 3 is integrally provided with the housing body 1 so as to close a portion near one end in a longitudinal direction of the open side. The access cover 2 is attached to an edge of the housing body 1 at another end in the longitudinal direction of the open side, in a rotatable manner via a hinge 2a. The access cover 2 is generally urged to be open by a restoring spring (not shown) The front cover 3 has a lock lever 10 provided with a protrusion 10a. The protrusion 10a engages with a tip end (a free end) of the access cover 2 to prevent the access cover 2 from being opened unintentionally.

When the lock lever 10 is slid against the resiliency of the spring, the protrusion 10a is released from the tip end of the access cover 2, the access cover 2 is rotated around a shaft (not shown) of the hinge 2a due to the resiliency of the restoring spring, and thus the access cover 2 is opened.

Figure 3:
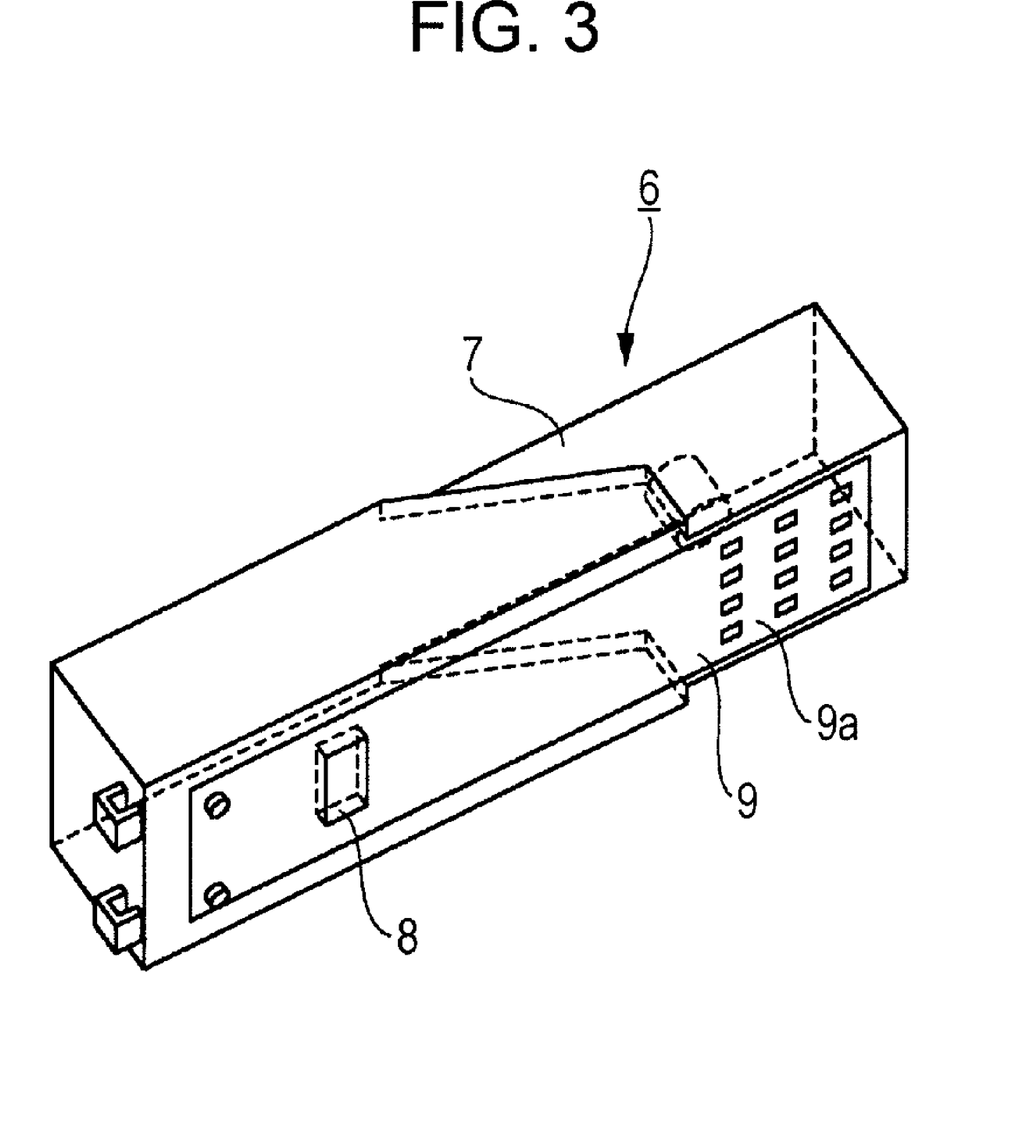
FIG. 3 is a perspective view showing a medicine discharge unit (a cartridge) provided in the inhaler shown in FIG. 1.

As shown in FIGS. 2 and 3, when the access cover 2 is opened, a medicine discharge unit (a medicine discharge cartridge) 6 and a mouthpiece (suction port) 4 are exposed. The medicine discharge unit 6 has a discharge head 8 and a medicine container (a medicine reservoir) 7 integrally disposed therein. The medicine discharge unit 6 and the mouthpiece 4 are supported by a guiding member 20 of the housing body 1 in a removable manner.

As shown in FIG. 3, the medicine discharge unit 6 includes the medicine container 7 that accommodates medicine, the discharge head 8 that discharges the medicine, and a member 9 having an electric connection surface 9a. The electric connection surface 9a is electrically connected to a battery that supplies power to a heater provided at the discharge head 8 to cause the heater to generate thermal energy. The battery may be a rechargeable secondary battery. As described above, the medicine container and the discharge head may be integrated in a form of a cartridge. Alternatively, the medicine container and the discharge head may be provided independently.

In the present invention, the medicine discharge portion (the discharge head) may have a desired discharge-pressure generating element. Examples of the discharge-pressure generating element may include an electrothermal transducer which applies thermal energy to medicine, and an electromechanical transducer which applies mechanical energy to medicine. In other words, examples of a method for discharging medicine may include a method which applies thermal energy to medicine using an electrothermal transducer and discharges the medicine from a discharge port (a thermal jet method), and a method which applies mechanical energy to medicine by utilizing an oscillating pressure of an electromechanical transducer (e.g., a piezoelectric element) and discharges the medicine from the discharge port. The method for discharging the medicine may be selected depending on the type of medicine, etc.

In the case where the thermal jet method is used, the diameter of the discharge port, the quantity of heat of a thermal pulse used during the discharging, and the size of a microheater as the electrothermal transducer may be accurately determined for each medicine discharge unit, thus enhancing reproducibility. Accordingly, a droplet size distribution may become narrowed. In addition, the manufacturing cost of the discharge head may be low, and such a discharge head may be applied to various small devices requiring frequent replacement of the discharge head. Because of this, a medicine discharge device using the thermal jet method is suitable particularly when the medicine discharge device is desired to be portable and convenient.

The medicine used for the present invention is not limited to medicine containing a medicinal compound that exhibits pharmacological and physiological actions. The medicine may contain a flavoring agent, a colorant, a pigment, etc., in addition to the medicinal compound. Also, the medicine may be liquid or powder.

A medical solution which is used for the present invention may be liquid medicine, or a liquid medium containing medicine. The medical solution may additionally contain a desired additive. The condition of medicine in liquid may be any one of dissolution, dispersion, emulsification, suspension, and slurry. The medicine may be suitable for use if it is equalized in the liquid.

When the medical solution is used as the medicine, the major component of the liquid medium may be water or an organic material. In particular, the major component may be water in view of administration of the medicine to a living body.

Figure 4:
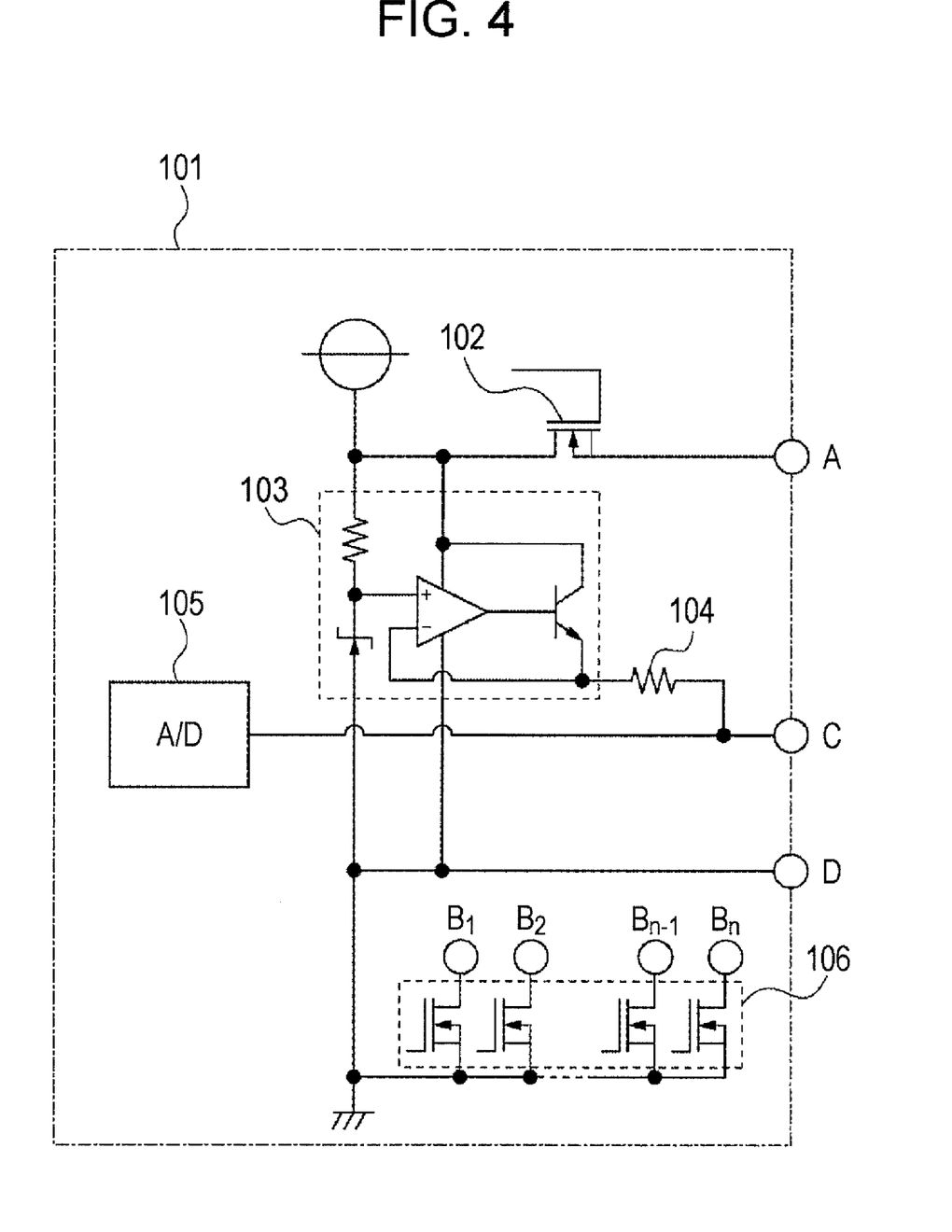
FIG. 4 is a diagram showing an internal circuit of the medicine discharge device according to an embodiment of the present invention.
Figure 5:
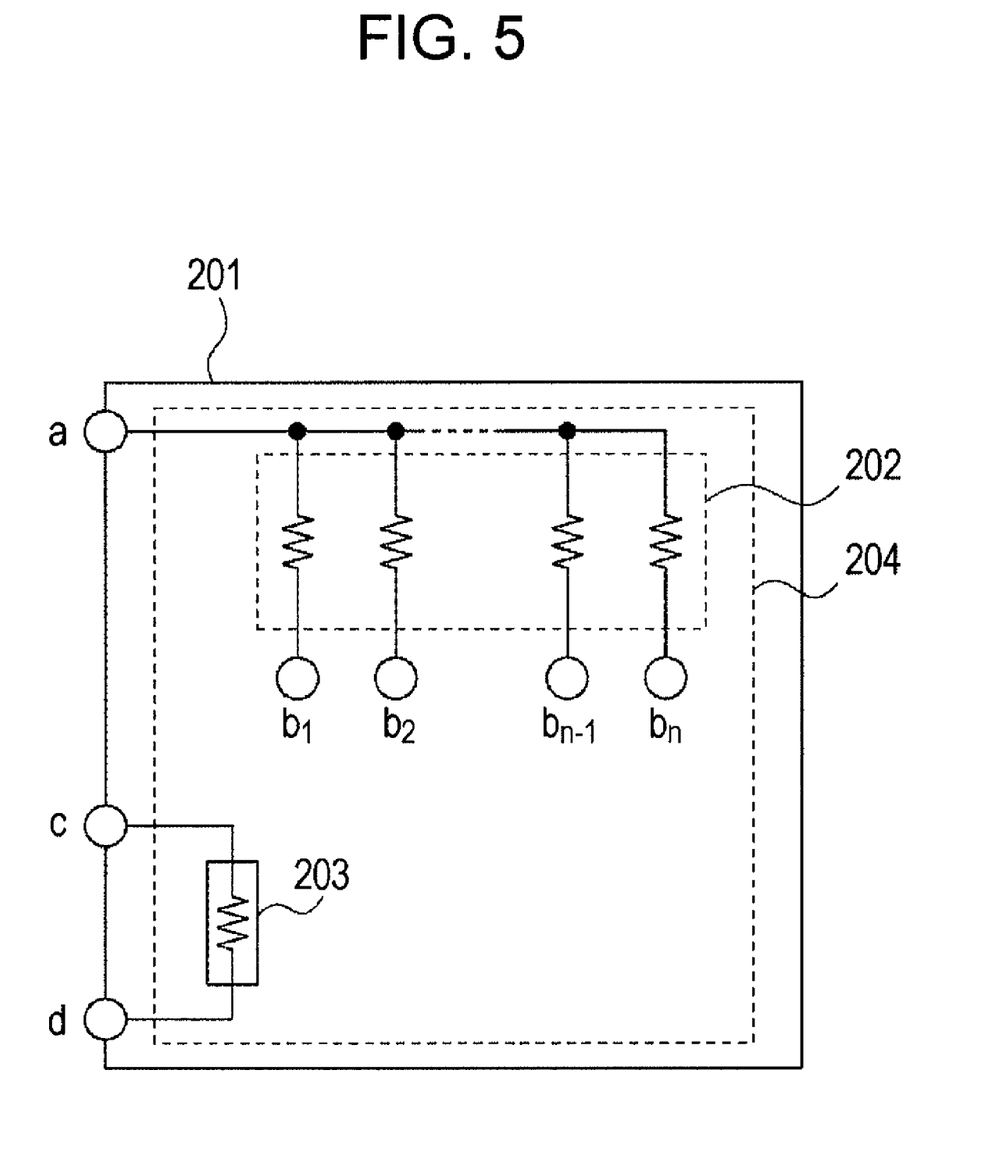
FIG. 5 is a diagram showing an internal circuit of a cartridge used for actual inhalation.
Figure 6A:
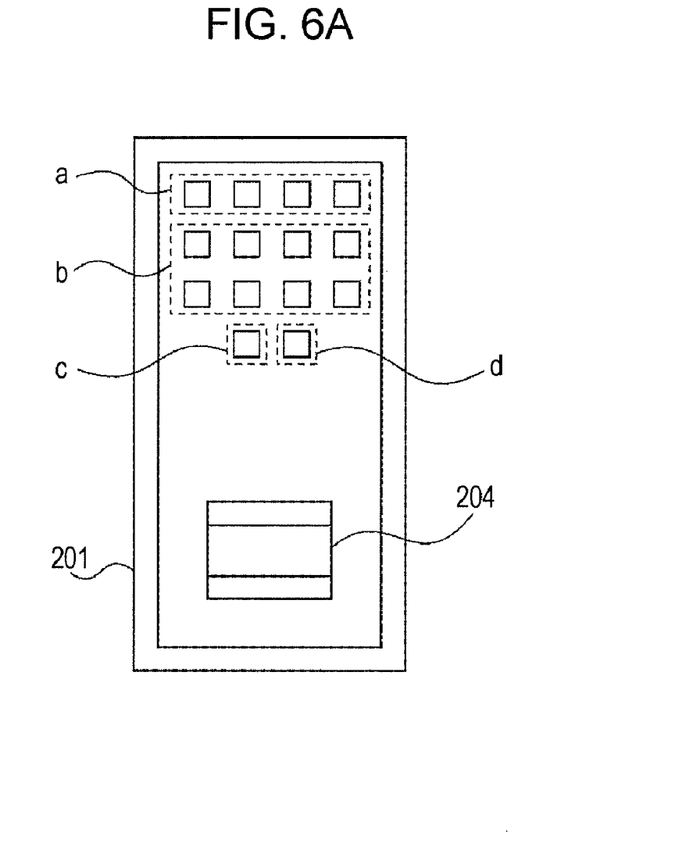
FIG. 6A is a front elevational view showing a side provided with a heater board of the cartridge shown in FIG. 5.
Figure 6B:
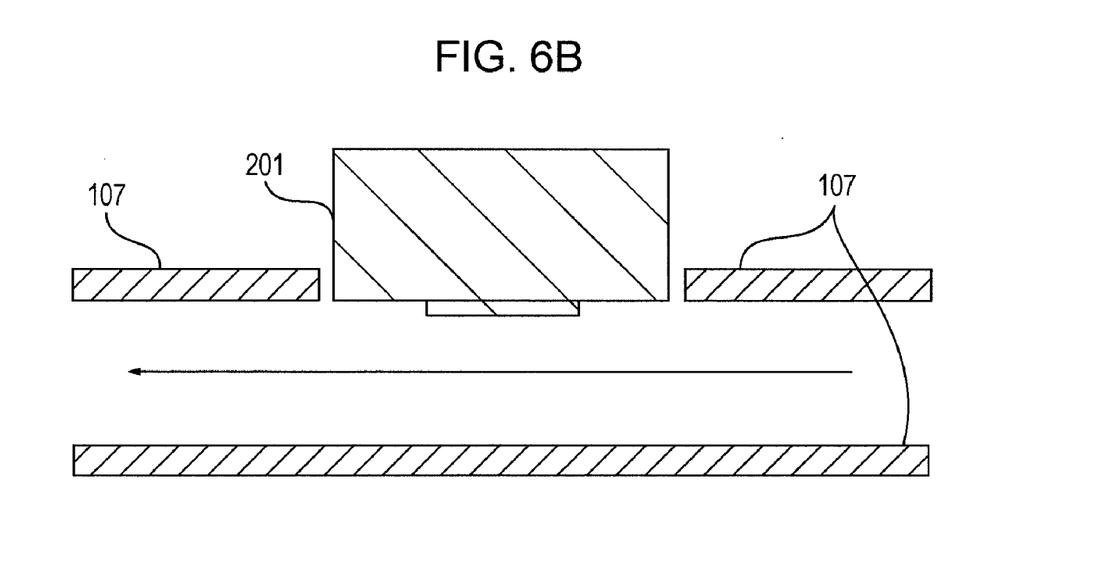
FIG. 6B is a cross-sectional view showing a channel when the cartridge shown in FIG. 5 is mounted to a device body of the medicine discharge device.
Figure 7:
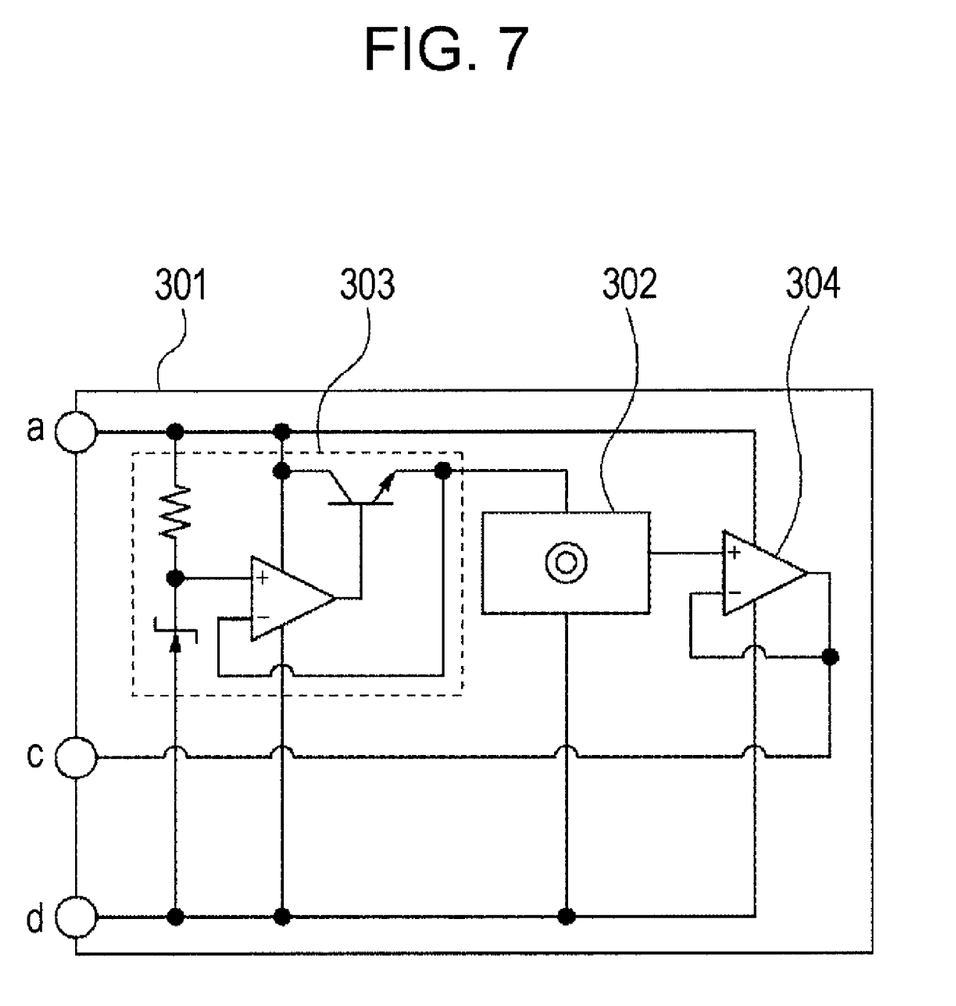
FIG. 7 is a diagram showing an internal circuit of an inhalation-training dummy cartridge according to an embodiment of the present invention.
Figure 8A:
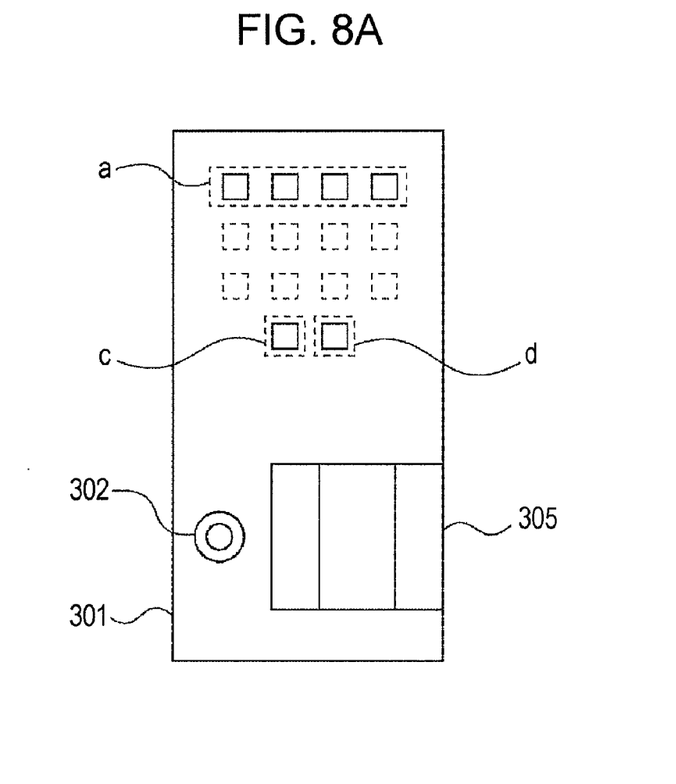
FIG. 8A is a front elevational view showing a side provided with a sensor element of the dummy cartridge shown in FIG. 7.
Figure 8B:
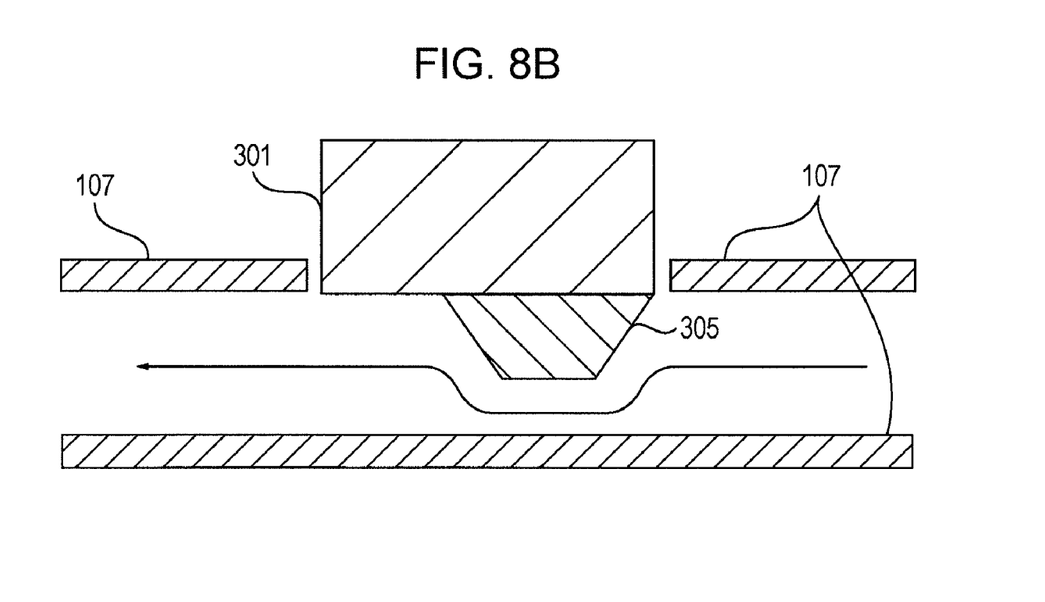
FIG. 8B is a cross-sectional view showing an air channel when the dummy cartridge shown in FIG. 7 is mounted to the medicine discharge device.

FIG. 4 is a diagram showing an internal circuit of the medicine discharge device according to an embodiment of the present invention. FIG. 4 illustrates a circuit provided in a body of an inhaler 101 (corresponding to reference character E shown in FIG. 1). FIGS. 5, 6A and 6B illustrate a cartridge 201 (corresponding to reference numeral 6 shown in FIGS. 1 to 3) that is mounted to the inhaler 101. FIGS. 7, 8A and 8B illustrate an inhalation-training dummy cartridge 301 that is mounted to the inhaler 101.

FIG. 5 is a diagram showing an internal circuit of the cartridge 201 used for actual inhalation. The cartridge 201 has a heater board 204 embedded therein. The heater board 204 has a heater 202 provided thereon. An electric pulse is applied to the heater 202, so that the medicine in a liquid chamber of the discharge head is heated, causing bubbles to be generated in the medicine, and is discharged as microdroplets from the discharge port communicated with the liquid chamber. Accordingly, the inhaler 101 may be used as a medicine inhaler by a user. The heater board 204 also has a temperature detecting element 203 provided thereon. The value of resistance of the temperature detecting element 203 characteristically varies with temperature. So, the temperature of the heater board 204 can be measured by applying a constant current to the temperature detecting element 203, and measuring the voltages at both ends thereof. While the temperature detecting element 203 is illustrated as a resistance, an effect similar to that of the resistance may be obtained by a diode whose forward voltage characteristically varies with temperature. The cartridge (6, 201) includes at least a medicine reservoir that accommodates the medicine, and a discharge portion. The cartridge is removable from the body of the inhaler (101 shown in FIG. 4).

Terminals A to D shown in FIG. 4 are respectively connected to terminals a to d shown in FIGS. 5, 6, 7, 8A and 8B. The internal circuit of the inhaler 101 includes embedded therein a power-control field-effect transistor (FET) 102, an FET 106 as a driving switch, a constant current circuit 103 as well as a resistance element 104, and an A/D converter 105. The power-control FET 102 supplies a supply voltage to the terminal a through the terminal A. The FET (the driving switch) 106 is connected to the terminal b through the terminal B to establish power distribution of the heater 202 provided in the cartridge 201. The constant current circuit 103 and the resistance element 104 supply a constant current to the temperature detecting element 203 connected to the terminal c through the terminal C. The A/D converter 105 converts the voltage of the terminal C from analog to digital to detect the voltage. The terminal D is connected to another terminal of the temperature detecting element 203 through the terminal d. The terminal D is grounded to a reference voltage source at low voltage. The terminal D supplies a constant current to the resistance element 104 when the cartridge 201 is mounted to the inhaler 101. While the constant current circuit 103 and the resistance element 104 are illustrated as a direct-current amplifier circuit, a three-terminal regulator or a constant-current diode may be alternatively used. The FET (driving switch) 106 supplies discharge signals for discharging the medicine, which is administered to the user, to the cartridge 201 through the terminals $B_1$ to $B_n$.

FIG. 6A is a front elevational view showing a side provided with the heater board 204 of the cartridge 201 shown in FIG. 5. FIG. 6B is a cross-sectional view showing a channel (corresponding to reference numeral 5 shown in FIGS. 1 and 2) when the cartridge 201 shown in FIG. 5 is mounted to the body of the inhaler 101. A channel wall 107 having an opening is provided in the inhaler 101. When the cartridge 201 is mounted to the inhaler 101, the heater board 204 of the cartridge 201 is fitted to the opening of the channel wall 107, so as to form a channel by closing the opening. The discharged medicine passes through the channel, and is inhaled by the user. At this time, the channel may be a straight profile to prevent the medicine from becoming adhered to the channel due to occurrence of turbulence.

FIG. 7 is a diagram showing an internal circuit of an inhalation-training dummy cartridge 301 according to an embodiment of the present invention. A source voltage is supplied to the dummy cartridge 301 through the terminals a and d. The dummy cartridge 301 has therein a sensor element 302 such as a pressure sensor constituted by a piezoelectric element or the like that detects a variation in pressure. In addition, a power supply circuit 303 for the sensor element 302, an operational amplifier 304 for amplifying output signals, etc., may be embedded in the dummy cartridge 301 if required in accordance with the specification of the sensor element 302, or the method for controlling the power of the inhaler 101. The output of the operational amplifier 304 is connected to the terminal c, and is input to the A/D converter 105 as a receiver circuit of the body of the inhaler 101. While the power supply circuit 303 for the sensor element 302 is illustrated as a direct-current amplifier circuit, a three-terminal regulator may be alternatively used. While the operational amplifier 304 is illustrated as a buffer amplifier, any desired circuit configuration may be employed. Depending on the circuit configuration employed, the operational amplifier 304 may be embedded in the inhaler 101.

FIG. 8A is a front elevational view showing a side provided with the sensor element 302 of the dummy cartridge 301 shown in FIG. 7. FIG. 8B is a cross-sectional view showing an air channel when the dummy cartridge 301 shown in FIG. 7 is mounted to the body of the inhaler 101. The profile of the dummy cartridge 301 is substantially equivalent to that of the cartridge 201. The dummy cartridge 301 may be mounted to the inhaler 101 instead of the cartridge 201. A pressure detector of the sensor element 302 is disposed at a position facing the air channel. Since the dummy cartridge 301 can be mounted to the body of the inhaler 101 for training instead of the cartridge 201, the dummy cartridge 301 does not require a medicine reservoir.

The dummy cartridge 301 is mounted to the inhaler 101, and the power-control FET 102 is turned ON, so that the sensor element 302 of the dummy cartridge 301 enters an enabled state. When the user performs an inhalation operation, the sensor element 302 detects the variation in pressure as an inhalation state, and transmits an output signal to the A/D converter 105 as the receiving circuit through the terminal C. The inhalation state of the user may be measured regardless of the presence of such a inhalation-detecting mechanism provided in the inhaler 101.

An optimal inhalation method is determined in accordance with the age, sex, symptom, prescribed amount of medicine, kind of medicine, and the like for each user of the inhaler 101. When the user does not inhale the medicine, the user may measure the inhalation state by using the dummy cartridge 301, compare the measured state with data representing an optimal inhalation method which has been registered in a memory of the inhaler 101, and evaluate the result. Accordingly, the user can perform training for the inhalation method on a daily basis without an instruction given by a professional such as a doctor or a pharmacist. At this time, the result of comparison with the optimal inhalation method and the evaluation thereof may be provided to the user, for example, by an image forming device or a sound output device. By having enough training for the inhalation on a daily basis, the user may learn the optimal inhalation method. This may improve or maintain intake efficiency of the medicine.

In addition, the sensor which accurately detects an inhalation pattern is not provided at the body of the inhaler 101, but is provided at the dummy cartridge 301. This may prevent an additional expensive function from being provided at the body of the inhaler 101, thereby simplifying the configuration of the inhaler 101. Further, the dummy cartridge 301 is mounted to the body of the inhaler 101 such that the position of the pressure detector of the sensor element 302 corresponds to the position of the discharge port of the discharge head when the cartridge 201 for the actual inhalation is mounted. Accordingly, the sensor may be disposed at or near the actual discharge portion. This realizes the detection of the optimal inhalation state (inhalation pattern).

Also, during the training for detecting the inhalation pattern, no medicine is discharged, thereby eliminating waste of the medicine.

Generally, the sensor element 302 tends to be expensive as it can detect a small pressure. Since no medicine is discharged during the use of the dummy cartridge 301, it is not necessary to consider the occurrence of turbulence or the adhesion of medicine. Due to this, a protrusion 305 may be provided upstream of the sensor element 302 so that the inhalation channel is narrowed to increase an airflow rate. This may cause a large negative pressure to be generated at the sensor element 302. The large negative pressure may enhance detection accuracy, and consequently, accurate measurement may be performed even with an inexpensive element. The sensor element 302 may be provided on the protrusion 305.

In the case where the dummy cartridge 301 is used, the terminals B and b need not be used because the medicine is not discharged. However, a dummy resistance equivalent to the heater 202 may be provided at the dummy cartridge 301 if the body of the inhaler 101 is provided with a circuit that performs installation detection and defective detection of the cartridge 201 by measuring resistance values between the terminals A and B. In this case, the inhaler 101 may detect the installation of the dummy cartridge 301 according to the dummy resistance being in an open state, or according to the combination of the resistance values. Alternatively, an output value of the operational amplifier 304 in a steady state may be increased as compared with the output voltage of the constant current circuit 103 to indicate the installation of the dummy cartridge 301. Or the combination of the above-described configurations may provide reliable determination between the cartridge 201 and the dummy cartridge 301.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2006-208500 filed Jul. 31, 2006, and No. 2007-150302 filed Jun. 6, 2007, which are hereby incorporated by reference herein in their entirety.

What is claimed is:

1. A medicine discharge device configured to discharge medicine to be administered to a user, said device comprising:
    an inhaler configured to allow the user to inhale the medicine, said inhaler including at least a mount portion configured to removably mount a medicine discharge cartridge and to removably mount an inhalation-training-cartridge different from said medicine discharge cartridge, said mount portion being configured to mount only one of said cartridges at a time, said medicine discharge cartridge having a medicine reservoir and a medicine discharge portion, said medicine reservoir configured to accommodate the medicine, said medicine discharge portion configured to discharge the medicine,
    wherein said mount portion is configured to removably mount said medicine discharge cartridge only when said inhalation-training cartridge is not mounted to said mount portion, and said mount portion is configured to removably mount said inhalation-training cartridge only when said medicine discharge cartridge is not mounted to said mount portion,
    wherein said inhalation-training cartridge includes a sensor configured to detect an inhalation state with no medicine discharged so that the user measures the inhalation state for training, and
    wherein said inhaler includes a receiving circuit configured to receive an output signal sent from said inhalation-training cartridge, said inhalation-training cartridge mounted at said mount portion.

2. A medicine discharge device configured to discharge medicine to be administered to a user, said device comprising:
    an inhaler including at least a mount portion and an inhalation channel, said mount portion configured to removably mount a medicine discharge cartridge and to removably mount an inhalation-training-cartridge different from said medicine discharge cartridge, said mount portion being configured to mount only one of said cartridges at a time, said medicine discharge cartridge having a medicine reservoir and a medicine discharge portion, said medicine reservoir configured to accommodate the medicine, said medicine discharge portion configured to discharge the medicine, said inhalation channel having an opening in which said medicine discharge portion is arranged when said medicine discharge cartridge is mounted,
    wherein said mount portion is configured to removably mount said medicine discharge cartridge only when said inhalation-training cartridge is not mounted to said mount portion, and said mount portion is configured to removably mount said inhalation-training cartridge only when said medicine discharge cartridge is not mounted to said mount portion,
    wherein said inhalation-training cartridge includes a sensor configured to detect an inhalation state with no medicine discharged so that the user measures the inhalation state for training,
    wherein said sensor is arranged at a position corresponding to the opening when said inhalation-training cartridge is mounted to said mount portion, and
    wherein said inhaler includes a receiving circuit configured to receive an output signal sent from said inhalation-training cartridge, said inhalation-training cartridge mounted at said mount portion.

3. The medicine discharge device according to claim 2, wherein said inhalation-training cartridge further comprises a protrusion having a profile that allows said inhalation channel to be narrowed when said inhalation-training cartridge is mounted to said mount portion.

4. The medicine discharge device according to claim 1, wherein said sensor is a pressure sensor.

5. An inhalation-training cartridge removably mountable onto an inhaler configured to allow a user to inhale medicine, wherein said inhaler includes a mount portion configured to removably mount a medicine discharge cartridge different from said inhalation-training cartridge only when said inhalation-training cartridge is not mounted to said mount portion, and is configured to removably mount said inhalation-training cartridge only when said medicine discharge cartridge is not mounted to said mount portion, said medicine discharge cartridge having a medicine reservoir and a medicine discharge portion, said medicine reservoir configured to accommodate the medicine, said medicine discharge portion configured to discharge the medicine,
    wherein said inhalation-training cartridge includes a sensor configured to detect an inhalation state with no medicine discharged so that the user measures the inhalation state for training, and
    wherein the sensor outputs a signal in accordance with the detected inhalation state.

6. The inhalation-training cartridge according to claim 5, further comprising a protrusion having a profile that allows said inhalation channel to be narrowed when said inhalation-training cartridge is mounted to said inhaler, airflow being generated in said inhalation channel when the user performs inhalation.

7. The inhalation-training cartridge according to claim 5, wherein said sensor is a pressure sensor.

8. The medicine discharge device according to claim 3, wherein the protrusion is positioned upstream of the sensor.

9. The medicine discharge device according to claim 3, wherein the sensor is positioned on the protrusion.

* * * * *